United States Patent [19]

Lake et al.

[11] 4,450,312

[45] May 22, 1984

[54] HYDROCARBON CONVERSION

[75] Inventors: Ivan J. S. Lake, Middlesbrough; Thomas V. Whittam, Darlinton, both of England

[73] Assignee: Imperial Chemical Industries PLC, London, England

[21] Appl. No.: 331,830

[22] Filed: Dec. 17, 1981

[30] Foreign Application Priority Data

Dec. 17, 1980 [GB] United Kingdom ............... 8040398

[51] Int. Cl.³ ..................... C07C 5/24; C07C 5/30
[52] U.S. Cl. ........................... 585/481; 423/326; 423/328
[58] Field of Search ............... 585/481, 482; 423/326

[56] References Cited

U.S. PATENT DOCUMENTS

| | | | |
|---|---|---|---|
| Re. 30,157 | 11/1979 | Burress | 585/411 |
| 3,702,886 | 11/1972 | Angauer et al. | 423/328 |
| 3,856,871 | 12/1974 | Haag et al. | 585/481 |
| 3,856,872 | 12/1974 | Morrison | 585/481 |
| 3,856,873 | 12/1974 | Burress | 585/481 |
| 4,208,305 | 6/1980 | Kovwenhoven et al. | 423/326 |
| 4,236,996 | 12/1980 | Tabak et al. | 585/481 |
| 4,269,813 | 5/1981 | Klotz | 423/326 |
| 4,331,641 | 5/1982 | Hinnenkamp et al. | 423/326 |
| 4,337,176 | 6/1982 | Boersma et al. | 423/326 |

FOREIGN PATENT DOCUMENTS

2831631  7/1978  Fed. Rep. of Germany ...... 423/326

OTHER PUBLICATIONS

Wu et al., J. Phys. Chem., 83, 2777 (1979).
Olson et al., J. Catalysis 61, 390 (1980).

*Primary Examiner*—Delbert E. Gantz
*Assistant Examiner*—A. Pal
*Attorney, Agent, or Firm*—Cushman, Darby & Cushman

[57] ABSTRACT

The process comprises isomerization, in the liquid or vapor phase, of a feed comprising a xylene or mixture of xylenes and optionally also containing up to 25% ethylbenzene using a catalyst comprising a novel crystalline aluminosilicate zeolite Nu-5.

10 Claims, No Drawings

HYDROCARBON CONVERSION

This invention relates to a process for the isomerisation of alkyl benzene hydrocarbons using a catalyst comprising a new zeolite material. The new zeolite material will be referred to hereinafter as "zeolite Nu 5" or simply "Nu5".

Zeolite Nu5 and its preparation are described in our copending U.S. patent application Ser. No. 331,832 filed even date herewith.

Zeolite Nu5 has a chemical composition, in terms of mole ratios of oxides, expressed by the formula $$0.5 \text{ to } 1.5 R_2O:Y_2O_3\text{:at least } 10XO_2\text{:0 to } 2000 H_2O$$

wherein R is a monovalent cation or 1/n of a cation of valency n, X is silicon and/or germanium, Y is one or more of aluminium, iron, chromium, vanadium, molybdenum, arsenic, manganese, gallium or boron and $H_2O$ is water of hydration additional to water notionally present when R is H, and has an X-ray pattern substantially as set out in Table 1 (as determined by standard technique using copper K $\alpha$ radiation).

Table 1 shows X-ray data for zeolite Nu5. The X-ray pattern is little affected by the type of cation present or by calcination or hydration.

TABLE 1

X-ray diffraction data for Nu-5

| As made Nu-5 | | Hydrogen Nu-5 | |
|---|---|---|---|
| dA | 100I/Io | dA | 100I/Io |
| 11.11 | 70 | 11.12 | 85 |
| 10.02 | 41 | 10.04 | 51 |
| 9.96 | 37 | 9.96 | 45 |
| 9.74 | 18 | 9.75 | 20 |
| 9.00 | 3 | 8.95 | 3 |
| 8.04 | 1 | 8.03 | 1 |
| 7.44 | 6 | 7.43 | 4 |
| 7.08 | 3 | 7.08 | 3 |
| 6.71 | 7 | 6.71 | 8 |
| 6.36 | 14 | 6.37 | 15 |
| 5.99 | 15 | 6.01 | 19 |
| 5.70 | 12 | | |
| 5.59 | 13 | 5.58 | 15 |
| 5.13 | 4 | 5.14 | 3 |
| 5.03 | 6 | 5.02 | 5 |
| 4.984 | 8 | 4.984 | 8 |
| 4.623 | 7 | 4.616 | 8 |
| 4.371 | 15 | 4.370 | 14 |
| 4.266 | 15 | 4.266 | 15 |
| 4.095 | 14 | 4.095 | 9 |
| 4.014 | 11 | 4.022 | 12 |
| 3.859 | 100 | 3.859 | 100 |
| 3.821 | 70 | 3.825 | 68 |
| 3.749 | 39 | 3.755 | 32 |
| 3.725 | 54 | 3.731 | 48 |
| 3.643 | 31 | 3.652 | 28 |
| 3.598 | 4 | 3.601 | 4 |
| 3.484 | 7 | 3.484 | 6 |
| 3.358 | 10 | 3.355 | 9 |
| 3.315 | 12 | 3.315 | 11 |
| 3.054 | 12 | 3.054 | 12 |
| 2.994 | 13 | 2.991 | 15 |
| 2.979 | 13 | 2.979 | 12 |
| 2.015 | 8 | 2.015 | 10 |
| 1.996 | 8 | 1.994 | 10 |

Within the above definition of chemical composition, the number of moles of $XO_2$ is typically in the range of 10 to 5000 and zeolite Nu5 appears to be most readily formed in a state of high purity when the number of moles of $XO_2$ is in the range 45 to 100.

This definition includes both freshly prepared zeolite Nu5 ("freshly prepared" means the product of synthesis and washing, with optional drying, as hereinafter described) and also forms of it resulting from dehydration, and/or calcination, and/or ion exchange. In freshly prepared zeolite Nu5, R may include an alkali metal cation especially sodium, and/or ammonium and hydrogen, and usually includes organic compounds as described below. These organic components are hereinafter referred to as A.

Since Nu5 is a zeolite, the organic component must be physically trapped within the crystal lattice. It can be removed by thermal or oxidative degradation or by displacement by suitable small molecules. The physically trapped basic material does not constitute part of the composition for the purposes of the definition. Thus a zeolite Nu-5 as made typically has the following molar composition:

$$0.7 \text{ to } 1.5 M_2O:1.0 \text{ to } 200A:Y_2O_3\text{:}10 \text{ to } 5000 XO_2\text{:}0 \text{ to } 2000 H_2O$$

wherein M is an alkali metal, ammonium or hydrogen.

The $H_2O$ content of freshly prepared zeolite Nu5 depends on the conditions in which it has been dried after synthesis.

In calcined forms of zeolite Nu5, R may be any cation including hydrogen since the organic component is burnt out in the presence of air, leaving hydrogen as the other balancing cation, or otherwise displaced prior to calcination.

Among the ion exchanged forms of zeolite Nu5 the ammonium ($NH_4^+$) is of importance since it can be readily converted to the hydrogen form by calcination. The hydrogen form can also be prepared directly by exchange with an acid. The hydrogen-form and forms containing metals introduced by ion exchange are described further in our co-pending U.S. patent application Ser. No. 331,832 filed even date herewith.

While the X-ray data for as made-, and hydrogen-, Nu-5 show a strong similarity to data for zeolite ZSM-5, there are very significant differences in line intensities in addition to extra lines present in Nu-5. These differences in line intensities are very substantial, and in scanning the spectrum of d-spaces, the intensity variations are very irregular, which suggests that the differences between the framework of Nu-5 and ZSM-5 are complex. These differences are further discussed and illustrated in our copending U.S. patent application Ser. No. 331,832 filed even date herewith.

According to the present invention a hydrocarbon conversion process comprises contacting a feed of an alkylbenzene or a mixture of alkylbenzenes under isomerisation conditions in the vapour or liquid phase with a catalyst comprising zeolite Nu5.

The catalyst used in the process of this invention may be zeolite Nu5 per se but in a preferred embodiment of the process zeolite Nu5 is used in the form of a physical mixture with a suitable diluent and/or binder, for example alumina, silica or a clay. Alumina is particularly preferred as a diluent, the amount of alumina present in the catalyst being preferably in the range 5 to 95% by weight based on total catalyst weight. The catalyst is conveniently used in the form of pellets, extrudates or other aggregates well known to those skilled in this art.

In the vapour phase, suitable isomerisation conditions for the process of this invention include a temperature in the range 100° to 600° C., preferably 200° to 450° C., and a pressure in the range 0.5 to 50, preferably 1 to 5, Kg/cm² absolute.

In the liquid phase embodiment of the process of this invention, suitable isomerisation conditions include a temperature in the range 0° to 350° C., a pressure in the range 1 to 200, preferably 5 to 70, Kg/cm² absolute and, in a flow system, a space velocity in the range 0.1 to 100, preferably 0.5 to 30, w/w hour, the higher flow rates being used at the higher temperatures. Optionally a diluent is present, suitably one or more of those having a critical temperature higher than the isomerisation temperature being used and including toluene, trimethylbenzene, naphthenes and paraffins. Preferably, the diluent if present, amounts to 1 to 90% of the feed to the isomerisation reaction. In the above mentioned forms of the process of this invention the catalyst preferably contains no hydrogenation/dehydrogenation component.

Optionally the isomerisation reaction is conducted in the presence of hydrogen. A suitable mole ratio of hydrogen to alkylbenzene feed lies in the range 1:1 to 30:1. If hydrogen is used, it is preferred that the catalyst should comprise a metal of Group VIII of the Periodic Table together with the zeolite. Preferably the metal of Group VIII is platinum or nickel. The amount of metal used preferably lies in the range 0.1 to 2% by weight of metal based on the total weight of catalyst. If desired, the catalyst may contain one or more additional metals, for example rhenium, suitably in the range 0.1 to 2% by weight based on the total weight of catalyst.

Preferably the alkylbenzene is a xylene, for example m-xylene for conversion to p-xylene, or a mixture of xylenes, possibly with ethylbenzene. The amount of ethylbenzene present will depend to some extent on the source of the xylene mixture but will usually lie in the range 0 to 25% by weight of the feedstock. However, we believe that the process of this invention is very suitable for at least partial destruction of the ethylbenzene in feedstocks containing relatively large amounts of ethylbenzene, say in the range 6 to 25% by weight of the feedstock.

The invention is illustrated by the following Example.

EXAMPLE

A sample of zeolite Nu5 prepared by the method described in Examples 1, 2 and 3 of our co-pending U.S. patent application Ser. No. 331,832 was formed into aggregates having diameters in the size range of 425 to 1000 μm. The zeolite's empirical formula was 0.11 Na₂O:Al₂O₃:62.6 SiO₂ and it contained 0.10% by weight sodium, 1.1% by weight aluminium and 35.8% by weight silicon.

The aggregated zeolite was charged to a glass reactor and heated in a stream of air at 500° C. for 16 hours. It was then cooled in a nitrogen stream to 400° C. A feedstock consisting mainly of C₈ aromatic hydrocarbons was then passed over the zeolite for 18 hours at a weight hourly space velocity of 8.8. Details of the feedstock composition and the composition of the product obtained are given in Table 2, all percentages being by weight.

TABLE 2

| Hours on line | Feedstock | 8 hours | 18 hours |
|---|---|---|---|
| Benzene % | 0.02 | 3.78 | 2.00 |
| Toluene % | 1.75 | 4.69 | 2.37 |
| Ethylbenzene % | 8.61 | 2.55 | 5.34 |
| Para-xylene % | 7.94 | 18.23 | 17.57 |
| Meta-xylene % | 50.92 | 42.48 | 44.45 |
| Ortho-xylene % | 25.54 | 20.19 | 21.73 |
| C₉⁺ Aromatics % | 3.86 | 6.71 | 5.19 |
| Para-xylene approach to equilibrium (%) | | 95.6 | 89.0 |
| Ethylbenzene loss (%) | | 70.4 | 38.0 |
| Xylene loss (%) | | 4.1 | 0.8 |

The results show that zeolite Nu-5 brings about the isomerisation of xylenes to close to equilibrium with little loss of xylenes. Simultaneous ethylbenzene loss is high.

We claim:

1. A process for isomerisation of an alkylbenzene or a mixture of alkylbenzenes, which method comprises contacting a feed of an alkylbenzene or a mixture of alkylbenzenes under isomerisation conditions in the vapor or liquid phase with a catalyst comprising zeolite Nu5 having a molar composition expressed by the formula:

$$0.5 \text{ to } 1.5 \text{ R}_2\text{O}:\text{Y}_2\text{O}_3:45 \text{ to } 100 \text{ XO}_2:0 \text{ to } 2000 \text{ H}_2\text{O}$$

wherein R is a monovalent cation or 1/n of a cation of valency n, X is silicon and/or gerdmanium, Y is either aluminum or aluminum and one or more of iron, chromium, arsenic, manganese and gallium, and H₂O is water of hydration additional to water notionally present when R is H, and having an X-ray diffraction pattern as set out in Table 1.

2. A process as claimed in claim 1 in which zeolite Nu-5 is used in the form of a physical mixture with a diluent and/or binder.

3. A process as claimed in claim 1 in which the process is carried out in the vapour phase under isomerisation conditions which include a temperature in the range 100° to 600° C. and a pressure in the range 0.5 to 50 Kg/cm² absolute.

4. A process as claimed in claim 1 in which the process is carried out in the liquid phase under isomerisation conditions which include a temperature in the range 0° to 350° C. and a pressure in the range 1 to 200 Kg/cm² absolute.

5. A process as claimed in claim 1 in which the isomerisation reaction is carried out in the presence of hydrogen.

6. A process as claimed in claim 5 in which the mole ratio of hydrogen to alkylbenzene feed is in the range 1:1 to 30:1.

7. A process as claimed in claim 5 in which the catalyst comprises a metal of Group VIII of the Periodic Table together with zeolite Nu-5.

8. A process as claimed in claim 7 in which the amount of metal of Group VIII is in the range 0.1 to 2.0% by weight.

9. A process as claimed in claim 1 in which the alkylbenzene is a xylene or a mixture of xylene isomers.

10. A process as claimed in claim 1 in which the alkylbenzene feed contains up to 25% by weight of ethylbenzene.

* * * * *